United States Patent [19]
Herdlicka

[11] Patent Number: 5,127,523
[45] Date of Patent: Jul. 7, 1992

[54] CONTAINER MADE OF PLASTIC FOR THE DISPOSAL OF DISPOSABLE MEDICAL UTENSILS AND DEVICES

[76] Inventor: Wolfgang Herdlicka, Senserbergstrasse 55 a,, D-8080 Fürstenfeldbruck, Austria

[21] Appl. No.: 592,945

[22] Filed: Oct. 3, 1990

[30] Foreign Application Priority Data

Oct. 4, 1989 [DE] Fed. Rep. of Germany ....... 3933177

[51] Int. Cl.⁵ .............................................. B65D 43/10
[52] U.S. Cl. ................................. 206/370; 206/459.5; 220/306; 220/908
[58] Field of Search .............. 206/366, 370, 807, 459; 220/256, 257, 258, 259, 306, 308, 908; 215/204, 263

[56] References Cited

U.S. PATENT DOCUMENTS

| | | | |
|---|---|---|---|
| 4,133,447 | 1/1979 | Bouchet | 220/306 |
| 4,231,480 | 11/1980 | Spransy . | |
| 4,337,869 | 7/1982 | Guinle | 220/256 |
| 4,453,646 | 6/1984 | Harrild | 220/258 |
| 4,520,926 | 6/1985 | Nelson | 206/366 |
| 4,682,700 | 7/1987 | Montgomery et al. . | |
| 4,877,150 | 10/1989 | Otto et al. | 206/366 |
| 4,940,157 | 7/1990 | Inagaki | 220/259 |
| 4,982,843 | 1/1991 | Jones | 206/366 |
| 5,031,768 | 7/1991 | Fischer | 220/306 |
| 5,042,679 | 8/1991 | Crowson et al. | 215/263 |

FOREIGN PATENT DOCUMENTS

| | | |
|---|---|---|
| 0221378 | 5/1987 | European Pat. Off. . |
| 8803416 | 5/1988 | European Pat. Off. . |
| 2312382 | 9/1974 | Fed. Rep. of Germany . |
| 7634267 | 6/1977 | Fed. Rep. of Germany . |
| 3317300 | 11/1984 | Fed. Rep. of Germany . |
| 8434243 | 2/1985 | Fed. Rep. of Germany . |
| 3505892 A1 | 8/1986 | Fed. Rep. of Germany . |
| 8710452 | 11/1987 | Fed. Rep. of Germany . |
| 3732975 A1 | 9/1988 | Fed. Rep. of Germany . |
| 8715839 | 2/1989 | Fed. Rep. of Germany . |
| 0326779 | 8/1989 | Fed. Rep. of Germany . |
| 8910567 | 12/1989 | Fed. Rep. of Germany . |
| 3823593 A1 | 1/1990 | Fed. Rep. of Germany . |
| 0976221 | 3/1951 | France ................ 206/306 |
| 3306 | of 1914 | United Kingdom . |
| 2044736 A | 10/1980 | United Kingdom . |

Primary Examiner—Jimmy G. Foster
Attorney, Agent, or Firm—Nikaido, Marmelstein, Murray & Oram

[57] ABSTRACT

The present invention relates to a container (1) made of plastic for the disposal of disposable medical utensils and devices after use. The container (1) comprises a closure (2) which is designed in such a way that the container (1) can be used as a packaging and transport container. To this end, the closure (2) is designed for two closed states which can be created successively, of which the first closed state is non-hermetic and permits the container to be opened, and of which the second closed state forms the hermetic, permanently closed state as required for the disposal of blood-soiled waste.

6 Claims, 4 Drawing Sheets

CONTAINER MADE OF PLASTIC FOR THE DISPOSAL OF DISPOSABLE MEDICAL UTENSILS AND DEVICES

The present invention relates to a container made of plastic for the disposal of disposable medical utensils and devices after use (blood-soiled waste), with a closure which hermetically seals the container and does not permit re-opening.

Disposable medical utensils and devices which, as so-called blood-soiled waste, have to be disposed of after use with particular safety precautions include oxygenators, tubes for heart-lung machines, dialysers and their tubes and similar devices which come into direct contact with the patient's blood during use. Special plastic containers for their disposal have been known in the prior art for at least ten years, which containers are supplied separately to hospitals and accommodate blood-soiled waste. Because of the danger of infection connected with them, these containers possess a closure which heremtically seals the container and which prevents re-opening of the container. The transport of such disposal containers with blood-soiled waste is subject to regulations pertaining to the transport of hazardous goods, as a result of which the containers have to be absolutely tight and sealed to prevent them from opening. The containers with blood-soiled waste are then disposed of by incinerating them in special incineration plants.

On the other hand the disposable medical utensils and devices are supplied in sterile packaging, the objects contained in this inner packaging being additionally stored in plastic trays which are in turn contained in an inner carton. In addition to this, an extremely strong outer carton is provided which encloses the unit. This costly packaging is necessary in order, for example, to prevent the tubes belonging to the equipment from being creased during gas sterilization when temperatures in the order of 45° C. can occur. It is usual for a number of such packaged units, stacked on pallets, to be subjected to sterilisation.

It is self-evident that the type of packaging used in the prior art for such disposable medical utensils and devices is exceedingly expensive, i.e. including the cost of the plastic tray, the cost of the inner carton and the cost of the heavy-duty outer carton and that, moreover, this type of packaging imposes a considerable burden on the environment, since it has to be incinerated after the disposable equipment has been used.

It is the object of the invention to, resolve this problem, the resolution of the problem being based on the recognition that the containers required in any case for the disposal of the blood-soiled waste can be used with appropriate modification as packaging for such sterile goods.

The object of the invention is therefore essentially resolved in that the container described in the introduction is designed in such a way that it can be used as a packaging and transport container for disposable utensils and devices by designing the closure to be used for two consecutive closed states, where the first closed state is not hermetic and permits the container to be opened and the second closed state is hermetic and permanent.

In such a container therefore, the disposable utensils and devices can easily be additionally packed for transport with their sterile packaging, since the first closed state permits the container to be opened and re-closed and, furthermore, sterilization is also possible, because the non-hermetic closed state ensures this. The sterile goods can therefore be sterilised together with their containers, also stacked on pallets, and then supplied to the customer in a container which, when the second closed state is used, also forms the disposal container. In this case, the cost of the container, which previously had to be purchased separately anyway, correspond essentially to the cost of the plastic tray, which was previously also required within the expensive packaging anyway. In this way a disposable medical utensil can be supplied right to the anteroom of the operating theatre in its delivery packaging, where after use the delivery packaging then forms the disposal container.

In a particularly preferred embodiment of the invention, the closure is in the form of a screw lid where the screw connection forms the first closed state, and the screw lid and container are provided with a positive locking device and seal which in the second closed state forms an hermetic, non-reopenable snap connection. Consequently, this container can be repeatedly opened and closed in its function as a delivery container by using the screw connection. For disposal purposes the hermetic, non-reopenable snap connection is formed.

This embodiment can be improved in detail by providing the screw lid with a downward-facing skirt which projects beyond the upper rim of the container, by producing the threads which form the screw connection with a great amount of play, and by designing the locking device in the form of mutually engaging annular rings on the skirt and the upper rim of the container. The large amount of play in the threads ensures that the sterilisation gas can easily penetrate the container even if a number of containers are stacked on top of each other on pallets. When using the packaging container for disposal, supplementary pressure is simply exerted on the lid from above, with the result that the annular rings are mutually engaged and seal the container in such a way that it is practically unopenable. This procedure is easily possible because of the fact that the plastic material is sufficiently flexible to permit one annular ring to slide over the other.

It is advantageous in particular in this respect for the annular rings to be located below the threads, since here in the free end region of the skirt, the flexibility of the lid is at its greatest.

It is further preferred that mutually opposed sealing surfaces and a tubular seal be located on the screw lid and the container, and that the distances between the annular rings and the sealing surfaces be such that once the snap connection has been made, the tubular seal is pressed together between the sealing surfaces. This ensures on the one hand that an absolutely hermetic seal is achieved and, on the other hand, the tubular seal generates a certain initial tension which holds the annular rings securely together.

In a particularly preferred modified embodiment of the invention, the closure device of the container is formed by two lids which can be connected with the container by means of one snap connection each, where one of the lids forms the first closed state and consequently has no seal and is formed with an openable snap connection, and where the second lid, which forms the second closed state, is provided with a seal and a non-reopenable snap connection which can, if required, be additionally locked. The container is thus delivered closed as a packaging and delivery container, after which, for disposal purposes, the second lid, which forms a non-reopenable and hermetic seal, is simply pressed down.

In this respect, it is preferable for the upper rim of the container to comprise an outwardly directed flange, for the lids to be of a box-type with slide walls engaging the flange, and for locking rails to be provided in the side walls of the lids which positively engage the flange in both closed states.

The lid locking rails are preferably triangular in cross-section, the locking rails of the first lid being rounded and formed with a comparatively obtuse crown angle, and the locking rails of the second lid being formed with a comparatively acute crown angle. As a result of this, the first lid can be removed from the container because of the flexible properties of the plastic material, while the second lid is practically impossible to remove from the container.

In an advantageous improvement to the invention, the seal on the second lid is located such that it becomes effective after the snap connection has been formed between the container and the second lid.

It is advantageous in detail for the lids to be positively or non-positively connectable with each other, where said connection can be re-opened. This enables the situation to be attained where both in the role of a packaging container and in the role of a disposal container there are no loose parts but rather the three component parts always form a manageable unit.

The invention can be improved in detail by providing supplementary locking tabs on the second lid which engage the flange on the container in such a way that the possibility of opening during disposal of the blood-soiled waste is practically excluded.

It is considered especially advantageous to form the two lids in different colours, so that a single glance is sufficient to establish whether the container holds waste which is to be disposed of or unused disposable medical utensils and devices.

Once the container according to the invention is also used at the same time as a packaging and delivery container and for sterilisation, it is further preferred to locate removable brackets in the container which prevent damage to or creasing of tubes during sterilisation.

This can be achieved in a preferred embodiment of the invention in that the container is formed in such a way that it tapers towards its base and that the brackets are formed as intermediate floors or similar with appropriate recesses, where said intermediate floors are held at various heights as appropriate on the walls of the container because of the container's conicity.

The invention is described below in detail with reference to the embodiments illustrated in the drawings, in which.

A first embodiment of the invention will be described initially with reference to FIGS. 1 to 5. Throughout this description the same references are used for the same parts or those performing the same function.

As shown, the object of the invention is a container 1 made of plastic, whose height can be between approximately 40 or 50 cm. and approximately 1.20 m., depending on the size of the objects to be contained. The container 1 is used on the one hand to dispose of disposable medical utensils and devices (not shown), such as oxygenators, tubes for heart-lung machines, dialysers and their tubes, etc., i.e. disposable utensils which are generally designated blood-soiled waste after use and have to be disposed of observing particular safety precautions.

At the same time, the container 1 serves as a packaging and transport container for the disposable utensils and devices, where for this purpose its closure designated 2 in general has two closed states which can be created successively. In the first closed state, the closure is non-hermetic and permits the container 1 to be opened, and in the second closed state, the container 1 is hermetically sealed after the blood-soiled waste has been placed inside it and does not permit re-opening.

Figure 1:
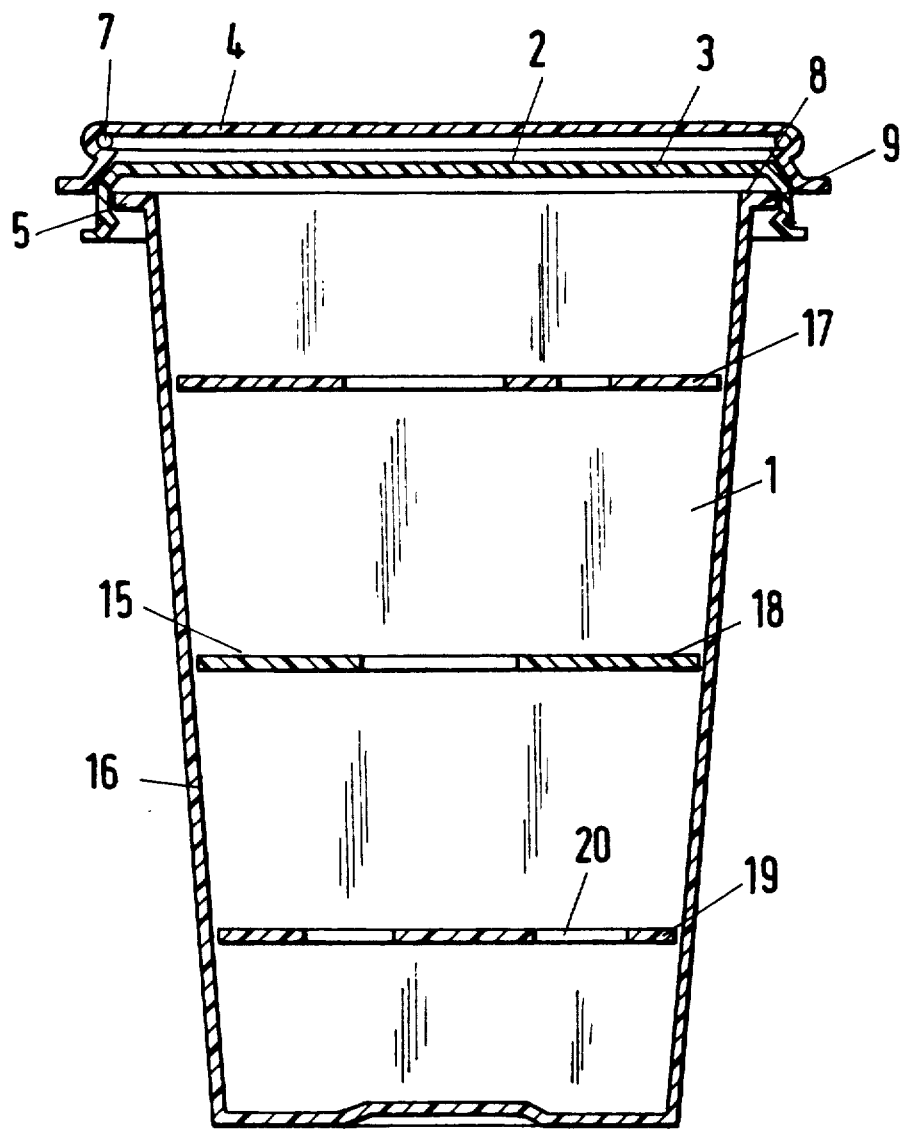
FIG. 1 shows a lateral section through a first embodiment of the container on a greatly reduced scale.
Figure 2:
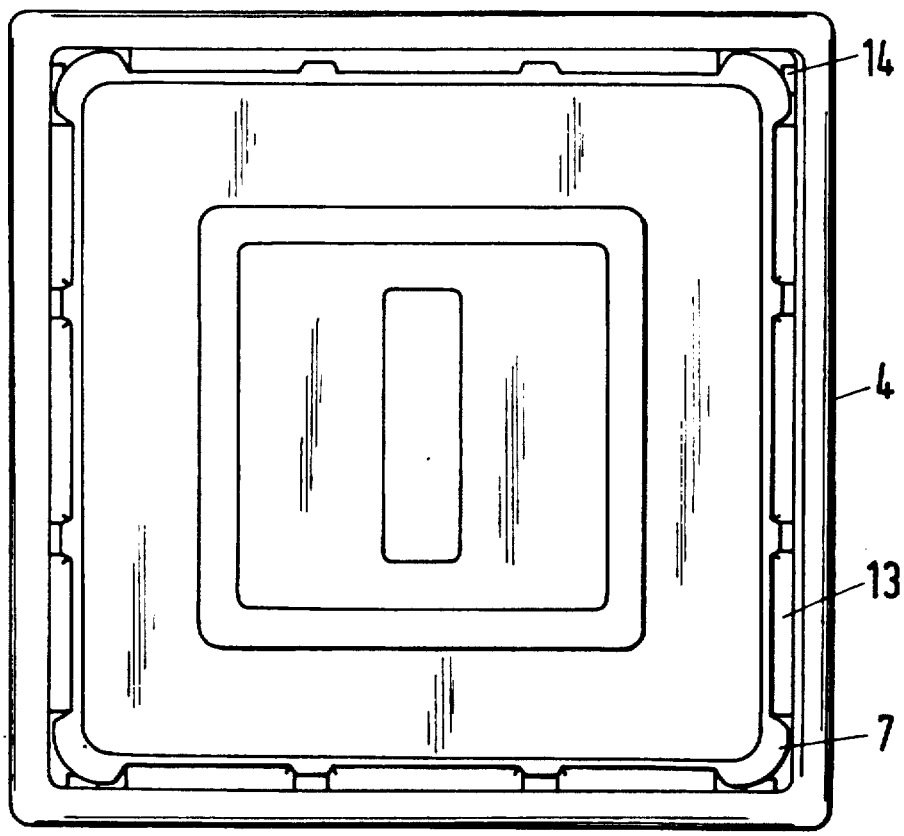
FIG. 2 shows an inverted plan view of the second lid for the second closed state.

In the embodiment illustrated in FIGS. 1 to 5, in which FIG. 1 shows the container in its role as a packaging and delivery container, these two closed states of the closure 2 are ensured by two lids 3 and 4, which fit on to the container 1, of which the first lid provides for the first closed state in that it is formed, without any particular seal, with a re-openable snap connection 5. The second lid 4, which—as shown in FIG. 1—is positively or non-positively connected to the first lid, where said connection can be re-opened, ensures the second hermetically sealed and non-reopenable closed state in that on the one hand it is provided with an unopenable snap connection 6, which can, if required, be additionally locked, and that on the other hand the lid 4 has a supplementary seal.

As shown, the container 1 is provided on its upper rim 8 with an outwardly directed flange 9. The lids 3 and 4 are of a box type and comprise side walls 10 and 11 which engage the flange 9.

The lids are also made of plastic, and in their side walls 10 and 11 distributed around the periphery of the respective lid 3 or 4, a number of locking rails 12 and 13 are formed which positively engage the flange 9 in the relevant closed state.

The locking rails 12 and 13 of the two lids 3 and 4 are each approximately triangular in cross-section. The locking rails 12 of the first lid 3 are rounded and formed with a comparatively obtuse crown angle which does not run parallel to the flange 9.

The locking rails 13 of the second lid 4 are formed with an acute crown angle by comparison with the locking rails 12 of the first lid 3, where the triangular cross-section is so aligned that the edge which engages the flange 9 runs parallel to the lower edge of said flange.

Figure 4:
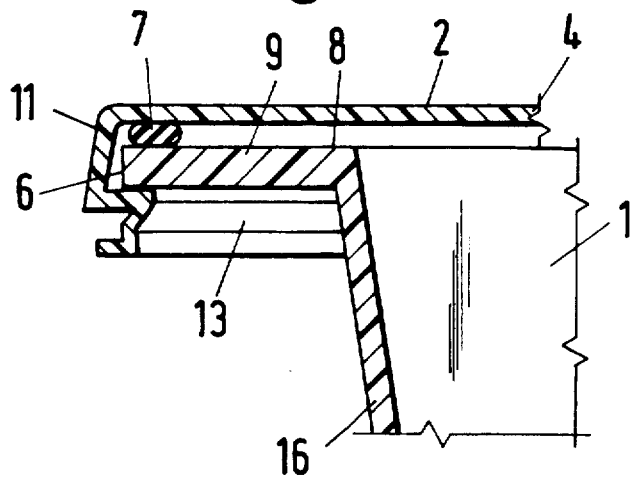
FIG. 4 shows a view corresponding to FIG. 3 of the snap connection of the second lid, with the container as shown in FIG. 1.

The seal 7, which encircles the lid 4 and which is preferably in the form of a tubular seal is located such that—as shown particularly in FIG. 4—it is pressed together between the upper edge of the flange 9 of the container 1 and the second lid 4 once the snap connection 6 has been made. In this way, the lid 4 is held against the container 1 under tension in such a way that is practically impossible to remove.

In the original use of the container 1 as a delivery container in which the lid 4 is pressed on top of the lid 3, the locking rails 13 of the lid 4 hold the untensioned seal 7 on the lid at the same time.

In a further improved embodiment, studs or other similar means can be provided in order to connect the two lids 3 and 4 to each other in such a way that they can be separated, with the result that the container always forms a unit with its closure 2 and that no loose lid has to be handled.

Figure 3:
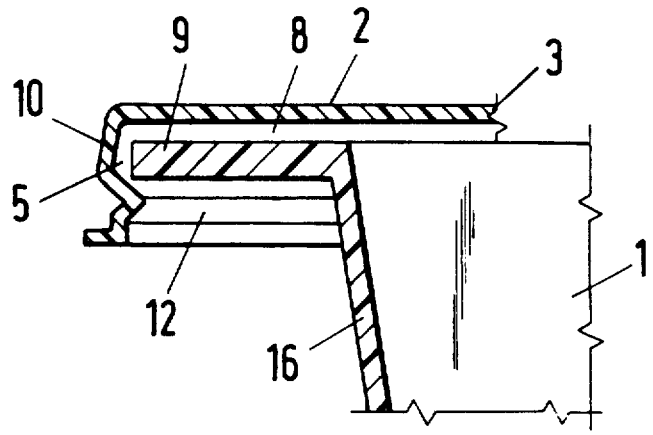
FIG. 3 shows a section through the snap connection between the first lid and the upper rim of the container as shown in FIG. 1.

It can be seen from FIG. 3 that there is enough play in the delivery state for the inside of the container 1 to be sterilised even if a number of containers are stacked on top of each other.

Figure 5:
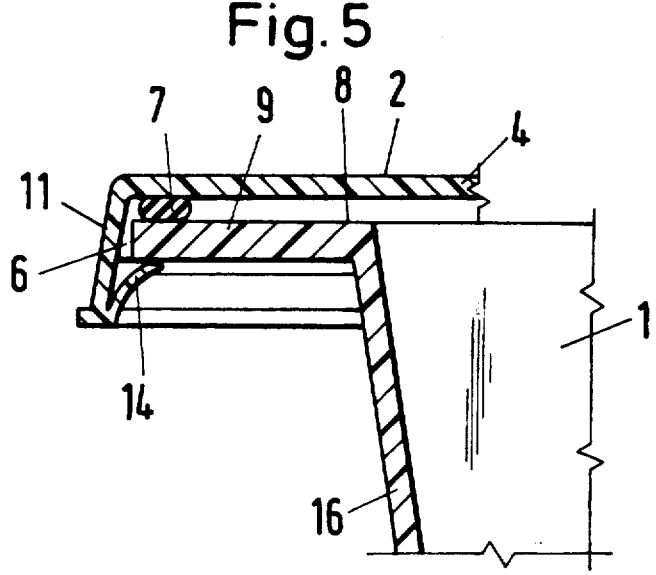
FIG. 5 shows a view corresponding to FIG. 4, which shows a supplementary locking device between the lid and the container.

As shown in FIG. 5, the second closed state of the container can be additionally locked by moulding projecting sprung locking tabs 14 made of the same plastic material as the lid 4 in addition to the locking rails, where said tabs also engage the flange 9 in the closed state.

In the embodiment illustrated in FIGS. 1 to 5, it is preferred that the two lids 3 and 4 be formed in different colours so that a single glance is sufficient to established whether the container is just a packaging for disposable medical utensils and devices or is intended for disposal.

A preferred detail is further apparent from FIG. 1, which consists in removable brackets 15 being provided in the container for the disposable objects, where said brackets prevent damage to said disposable objects during sterilisation or transport. To this end, the container 1 is formed in such a way that it tapers toward its base, and the brackets 15 re formed as intermediate floors 17, 18 or similar, with appropriate recesses 20, where said intermediate floors after appropriate sizing are held at various heights because of the conicity of the container 1.

Figure 6:
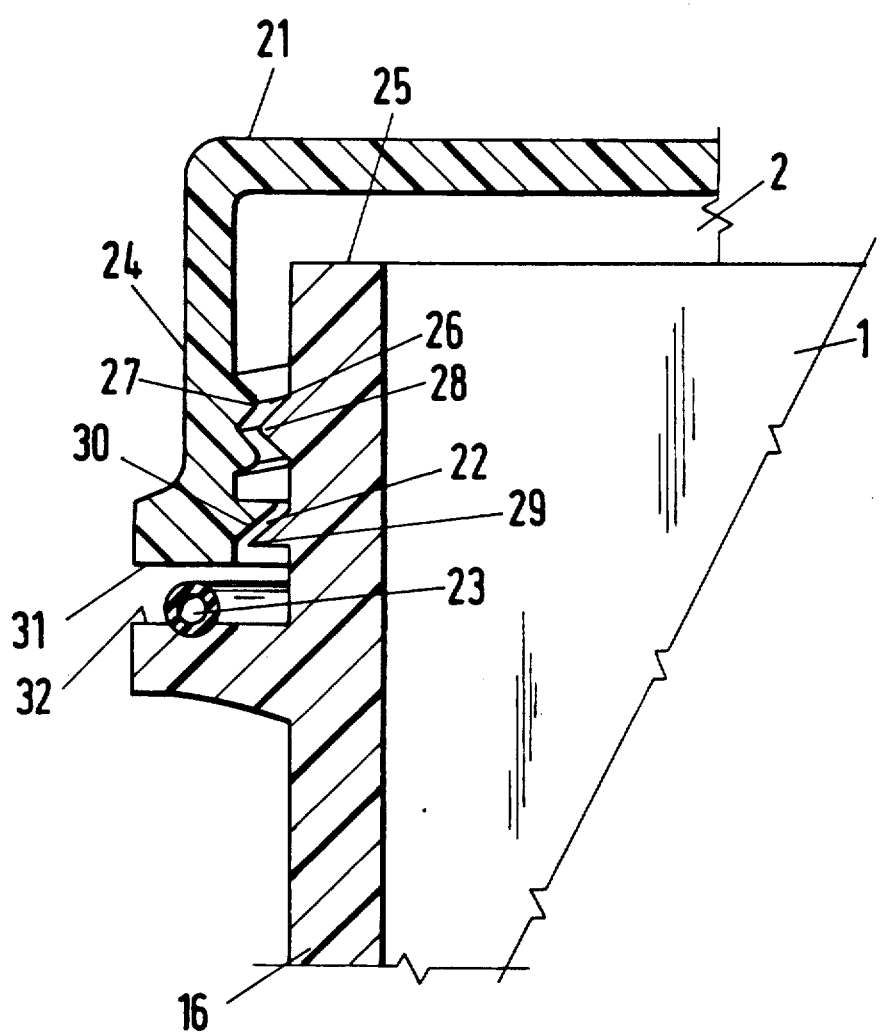
FIG. 6 shows a section through a second embodiment of the container, in which only part of the container closure is represented.

FIG. 6 of the drawings shows a modified embodiment of the invention in a representation corresponding to FIGS. 3 to 5, in which both closed states can be achieved by using a single lid.

To this end, the closure 2 is in the form of a screw lid 21. The screw connection 26 guarantees the first closed state, in which the container 1 is not hermetically sealed and is closed in such a way that it can be re-opened.

Positively engaging locking devices 22 and a seal 23 are provided on the screw lid 21 and the container 1, which guarantee the second state by producing a snap connection which cannot be re-opened.

As illustrated, the screw lid 21 comprises a downward-facing skirt 24, which projects beyond the upper rim 25 of the container 1. The threads 27, 28 which form the screw connection 26 are designed with a great amount of play in order to ensure that the sterilization gas penetrates the container 1 when it is used as a delivery container.

The locking devices 22 are designed in the form of mutually engaging annular rings 29, 30 on the skirt 24 and the upper rim 25 of the container 1, where said locking devices 22 have a triangular cross-section and mesh, when in the second closed state, with almost horizontal flanks.

The annular rings 29 and 30 are located below the threads 27 and 28 so that when the container 1 is being used for disposal, the annular ring 30 of the lid simply has to be pressed from over the annular ring 29.

In addition, mutually opposed sealing surfaces 31 and 32 are located on the screw lid 21 and the container 1 around the container 1, and a tubular seal 33 is located between these sealing surfaces. The distances between the annular rings 29 and 30 and the sealing surfaces 31 and 32 are chosen such that once the snap connection has been made, the tubular seal 33 is pressed together between the sealing surfaces 31 and 32.

In all the embodiments of the invention, the invention, the lids and also the containers can be manufactured in varying wall thicknesses in accordance with different requirements. In the embodiment according to FIGS. 1 to 5, the first lid can be made comparatively thin.

All the features and advantages of the invention arising from the description, claims and drawings, including design and spatial configurations, can be characteristics of the invention both in themselves and in any desired combination.

I claim:

1. A plastic container for the packaging, transportation and storage of disposable medical utensils and devices and for the packaging and disposal thereof after use and a closure for hermetically sealing said container and for preventing re-opening of said container after hermetically sealing characterized in that said closure has a first closed state in which said container is non-hermetically sealed and said container can repeatedly be opened, closed, re-opened and reclosed and a second closed state in which said container is hermetically sealed and premanently closed, said closure being formed by two lids connected to said container by means of a common snap, a first of said lids forming said first closed state having an openable snap connection and a second of said lids forming said second closed state having a seal and a non-openable snap connection, said container having, on its upper rim, an outwardly directed flange, said first and second lids are of a box type with side walls for engagement with said flange, and locking rails in said side walls of said lids for positively engaging said flange in both closed states.

2. Container as claimed in claim 1, wherein the locking rails (12, 13) of the first and second lids (3, 4) have an angular surface in cross-section, that the locking rails (12) of the first lid (3) are rounded and formed with a comparatively obtuse crown angle and that the locking rails (13) of the second lid (4) are formed with a comparatively acute crown angle.

3. Container as claimed in any one of claims 1 and 2, characterised in that the seal (7) on the second lid (4) is located in such a position that it becomes effective after the snap connection has been formed between the container (1) and the second lid (4).

4. Container as claimed in claim 1, characterised in that locking tabs (14) which engage the flange (9) are provided onthe second lid (4).

5. Container as claimed in claim 1, characterised in that the lids (3, 4) are formed in different colours.

6. Container as claimed in claim 1, characterised in that the container (1) is formed in such a way that it tapers towards its base and that the brackets (15) are formed as intermediate floors (17, 18, 19) or similar, provided with appropriate recesses (20), where said intermediate floors (17, 18, 19) are held at various heights on the walls (16) of the container (1) because of the container's conicity.

* * * * *